United States Patent [19]
Yates et al.

[11] Patent Number: 5,914,099
[45] Date of Patent: Jun. 22, 1999

[54] PREVENTION OF TOOTH LOSS BY THE ADMINISTRATION OF ALENDRONATE OR ITS SALTS

[75] Inventors: Ashley John Yates, Westfield; David B. Karpf, Edison, both of N.J.

[73] Assignee: Merck & Co., Inc., Rahway, N.J.

[21] Appl. No.: 08/952,067

[22] PCT Filed: May 8, 1996

[86] PCT No.: PCT/US96/06505

§ 371 Date: Nov. 4, 1997

§ 102(e) Date: Nov. 4, 1997

[87] PCT Pub. No.: WO96/35407

PCT Pub. Date: Nov. 14, 1996

Related U.S. Application Data

[63] Continuation of application No. 08/439,749, May 12, 1995, abandoned.

[51] Int. Cl.$^6$ ............................. A61K 7/16; A61K 31/66; A61K 33/42
[52] U.S. Cl. ........................... 424/49; 514/108; 514/900; 514/902
[58] Field of Search .......................................... 424/49–88

[56] References Cited

U.S. PATENT DOCUMENTS

| | | | |
|---|---|---|---|
| 4,621,077 | 11/1986 | Rosini et al. | 514/108 |
| 4,922,007 | 5/1990 | Kieczykowski et al. | 562/13 |
| 5,019,651 | 5/1991 | Kieczykowski | 562/13 |
| 5,270,365 | 12/1993 | Gertz et al. | 514/108 |
| 5,358,941 | 10/1994 | Bechard et al. | 514/102 |
| 5,366,965 | 11/1994 | Strein | 514/102 |
| 5,409,911 | 4/1995 | Tyler et al. | 514/91 |
| 5,431,920 | 7/1995 | Bechard | 424/480 |
| 5,462,932 | 10/1995 | Brenner et al. | 514/108 |

OTHER PUBLICATIONS

Krook et al., Cornell Vet. vol. 62 (1972), pp. 371–376, "Human periodontal disease and osteoporosis".
Groen et al., J. Periodontol., vol. 39 (1978), pp. 19–23, "Chronic destructive periodontal disease in patients with presinile osteoporosis".
Baxter, Quintessence Int'l, vol. 18 (1987), pp. 427–429, "Osteoporosis: Oral manifestations of a systemic disease".
Daniell, Arch. Int. Med., vol. 143, (1983), pp. 1678–1682, "Postmenopausal Tooth Loss: Contributions to edentulism by osteoporosis and cigarette smoking".
Hunt et al., Amer. J. of Public Health, vol. 78 (1988), pp. 1330–1332, "Incidence of tooth loss among elderly Iowans".
Henrikson et al., J. of Oral Rehabilitation, vol. 1 (1974), pp. 67–74, "The mandible and osteoporosis".
Glickman, Clin. Periodontology, 3rd ed. (1964), pp. 363–392.

*Primary Examiner*—Shep K. Rose
*Attorney, Agent, or Firm*—Anthony D. Sabatelli; Melvin Winokur

[57] ABSTRACT

Alendronate, a bisphosphonate can prevent tooth loss not necessarily associated with periodontal disease. Preferably, alendronate (or a pharmaceutically acceptable salt thereof) is given daily for an extended period of time.

6 Claims, No Drawings

PREVENTION OF TOOTH LOSS BY THE ADMINISTRATION OF ALENDRONATE OR ITS SALTS

CROSS REFERENCE TO RELATED APPLICATIONS

This is a U.S. National Phase Application of International Patent Application No. PCT/U.S. 96/06505, filed May 8, 1996, which is a continuation of U.S. paatent application Ser. No. 439,749, filed May 12, 1995, now abandoned.

DESCRIPTION OF THE INVENTION

This invention relates to a method of preventing tooth loss by the administration of alendronate or a pharmaceutically acceptable salt thereof.

BACKGROUND OF THE INVENTION

Alendronate, 4-amino-1-hydroxybutylidene- 1,1-bisphosphonic acid, and its pharmaceutically acceptable salts are known to be useful in the treatment of osteoporosis. See, for example U.S. Patent 4,621,077. It has also been used experimentally to treat alveolar bone loss associated with periodontitis and periodontal disease, as set forth in U.S. Pat. No. 5,270,365.

Alveolar bone of the mandible and maxilla serves as the primary foundation for tooth support. While alveolar bone is generally subject to metabolic and other systemic diseases of the skeleton, there has been relatively little work on the occurrence, progression, or impact of systemic osteoporosis on alveolar bone, although such a relationship may exist. Mandibular bone loss has been correlated with systemic bone loss, and it has been reported that tooth loss is exacerbated by osteoporosis.

Osteoporosis of the jaw may have a relationship to tooth loss. Alveolar maxillary bone and mandibular bone may be highly susceptible to osteoporosis in those who have already lost teeth, either due to disuse or changing mechanical forces. Osteoporosis of the maxilla is accompanied by an increase in size of the paranasal sinuses, which in dentate persons can cause the maxillary antrum to extend below the roots of posterior teeth, possibly causing severe referred pain in these teeth, tooth mobility, and increased periodontal pocketing. The latter can in turn, lead to loss of crestal bone and tooth loss. If teeth are lost, many persons are now receiving dental implants, prostheses anchored by metal pillary in alveolar bone. Success of this process may also depend in part on the structural integrity of the bone.

Further it has been suggested that there is a relationship between periodontal disease and osteoporosis. However, it has not been shown that compounds which can treat osteoporosis may be effective in preventing tooth loss which is not associated with periodontal disease.

DETAILED DESCRIPTION OF THE INVENTION

This invention relates to a method of preventing tooth loss not necessarily associated with periodontal disease in a human by administering an effective amount of alendronate, or a pharmaceutically acceptable salt thereof over an extended time.

It has been found, in accordance with this invention that administration of alendronate or a pharmaceutically acceptable salt thereof to patients can result in fewer patients who experience tooth loss, as compared with patients who have not received alendronate. Further, in accordance with this invention, administration of alendronate can result in fewer numbers of teeth lost in patients receiving alendronate and who experience tooth loss, as compared with patients who do not receive alendronate. Thus another aspect of this invention is a method of lessening the risk of tooth loss by administering alendronate or a pharmaceutically acceptable salt thereof.

For purposes of this specification and claims, the following definitions apply:

Extended time: a period of time greater than two years, preferably greater than three years.

Effective amount: a dosage of alendronate (or a pharmaceutically acceptable salt thereof) required to either (a) prevent progression of osteoporosis in the mandible or maxilla so that less tooth loss occurs than in the absence of alendronate; or (b) prevent osteoporosis from occurring in the mandible or maxilla so that less tooth loss occurs than in the absence of alendronate.

In accordance with this invention, alendronate may be given to patients who are either suffering from osteoporosis or who do not have this underlying disease.

It may be helpful to administer alendronate or its pharmaceutically acceptable salt for an extended time in order for the beneficial effects to occur. This is particularly so for patients who are already experiencing osteoporosis, i.e. have a bone mineral density (BMD) less than about 2.0 standard deviations below the normal peak BMD. Thus, in one aspect of this invention, alendronate is administered to osteoporotic patients substantially daily for a period of greater than two years, and preferably greater than three years.

Patients preferably will receive alendronate substantially daily in order for the effect to be observable. This means that the patient will receive alendronate at least one-half of the days in a treatment period, with the treatment period lasting at least one year, and is preferably longer, up to and exceeding three or more years. In a preferred embodiment, the patient will receive alendronate substantially daily for at least three years in order to experience the greatest benefit. It is envisioned that a patient receiving such a long-term therapy may experience occasional periods when alendronate is not administered; but since alendronate has some persistant activity in the bone, this is considered within the scope of the invention provided that the patient receives alendronate at least one-half of the days in the preceding six month period. Also, it is within the scope of this invention that the alendronate be administered on a cyclical regime, i.e., the patient may receive alendronate for a given period of time, i.e., one to six months, then may be taken off the alendronate (and may or may not be given additional bone-promoting or bone absorption-inhibiting agents, and/or hormonal therapy) for a second period of time, and returned to alendronate therapy.

Alendronate may be prepared according to any of the processes described in U.S. Pat. Nos. 5,019,651, 4,992,007, and U.S. application Ser. No. 08/286,151, filed Aug. 4, 1994, each of which is hereby incorporated by reference. The pharmaceutically acceptable salts of alendronate include salts of alkali metals (e.g., Na, K), alkali earth metals (e.g. Ca), salts of inorganic acids, such as HCl and salts of organic acids such as citric acid and amino acids. Sodium salt forms are preferred, particularly the monosodium salt trihydrate form.

The compounds of the present invention can be administered in oral dosage forms such as tablets, capsules (each of which includes sustained release or timed release formulations), pills, powders, granules, elixirs, paste, tinctures, suspensions, syrups, emulsions and zydis. Likewise they may be administered in an intravenous (bolus or infusion), intraperitoneal, subcutaneous, or intramuscular form, all using forms well known to those of ordinary skill in the pharmaceutical arts. An effective but non-toxic amount of the compound desired can be used as a tooth loss prevention agent.

The dosage regime utilizing the claimed method is selected in accordance with a variety of factors including age, weight, sex, and medical condition of the patient; the severity of the condition to be treated; the route of administration; the renal and hepatic function of the patient; and the particular compound or salt thereof employed. An ordinarily skilled physician or clinician can readily determine and prescribe the effective amount of the drug required to prevent tooth loss.

Oral dosages of the present invention will range from between 0.05 mg per kg of body weight per day (mg/kg/day) to about 1.0 mg/kg/day. Preferred oral dosages in humans may range from daily total dosages of about 2.5–50 mg/day over the effective treatment period, and a preferred amount is 2.5, 5, or 10 mg/day.

Alendronate may be administered in a single daily dose or in a divided dose. It is desirable for the dosage to be given in the absence of food, preferably from about 30 minutes to 2 hours prior to a meal, such as breakfast, to permit adequate absorption.

In the methods of the present invention, the active ingredient is typically administered in admixture with suitable pharmaceutical diluents, excipients or carriers (collectively referred to herein as "carrier materials") suitably selected with respect to the intended form of administration, i.e. oral tablets, capsules, elixirs, syrups and the like and consistent with conventional pharmaceutical practices. For example, for oral administration in the form of a tablet or capsule, the active ingredient can be combined with an oral, non- toxic, pharmaceutically acceptable inert carrier such as lactose, starch, sucrose, glucose, methyl cellulose, magnesium stearate, mannitol, sorbitol cros-carmellose sodium and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture of active ingredient(s) and inert carrier materials. Suitable binders may include starch, gelatin, natural sugars such as glucose, anhydrous lactose, free-flow lactose, beta-lactose, and corn sweeteners, natural and synthetic gums, such as acacia, tragacanth or sodium alginate, carboxymethyl cellulose, polyethylene glycol, waxes, and the like. Lubricants used in these dosage forms include sodium oleate, sodium stearate, magnesium stearate, sodium benzoate, sodium acetate, sodium chloride and the like. A particularly preferred tablet formulation is that described in U.S. Pat. No. 5,358,941, which is hereby incorporated by reference.

The compounds used in the instant method may also be coupled with soluble polymers as targetable drug carriers. Such polymers can include polyvinylpyrrolidone, pyran co-polymer, polyhydroxylpropyl-methacrylamide and the like.

The following non-limiting Examples are presented to further illustrate the invention.

EXAMPLE 1

Tooth Loss in Random Population

Women enrolled in this study are post menopausal, in good general health and are between 45–59 years old and have been selected randomly from a target population who live in a defined geographical area. No more than 10% of the participants has any incidence of osteoporosis evident on baseline spinal dual-energy X-ray densitometry.

Each subject is randomized to either placebo, alendronate low dose (ALN 2.5 mg per day), alendronate high dose (ALN 5 mg per day) or open labeled estrogen/progestin (E/P). The estrogen/progestin group (in the United States) will receive the conjugated estrogen PREMARIN® (0.625 mg per day) and the medroxyprogesterone acetate PROVERA® (2.5 mg per day) taken continuously throughout the calendar month. Outside the United States, the estrogen/progestin group will receive micronized 17β-estradiol and norethisterone acetate (Trisequens) as a cyclical regimen.

All subjects who have a calcium intake of less than 500 mg per day will be advised to increase their calcium intake (either by diet or supplements) to above this level. Distribution of the groups is shown in TABLE 1. Treatment groups is given in TABLE 2.

TABLE 1

TREATMENT GROUPS

| GROUP | TREATMENT | STRATUM 1 N | STRATUM 1 N/Site* | STRATUM 2 N | STRATUM 2 N/Site* | Total |
|---|---|---|---|---|---|---|
| A | Placebo | 150 | 35–40 | 300 | 70–80 | 450 |
| B | ALN** 2.5 mg | 150 | 35–40 | 300 | 70–80 | 450 |
| C | ALN 5 mg | 150 | 35–40 | 300 | 70–80 | 450 |
| D | E/P*** | 150 | 35–40 | — | — | 150 |
| TOTAL | | 600 | 140–160 | 900 | 210–240 | 1500 |

*Estimate
**ALN = alendronate
***E/P = estrogen/progestin

TABLE 2

STUDY SCHEMA

| | | YEAR OF STUDY | | |
|---|---|---|---|---|
| GROUP | N | 1 and 2 | 3 and 4 | 5 and 6 |
| A | 450 | Placebo | Placebo | ALN* OD**; R***; and Placebo |
| B1 | 150 | ALN 2.5 mg | ALN 2.5 mg | ALN 2.5 mg |
| B2 | 150 | ALN 2.5 mg | ALN 2.5 mg | Placebo |
| B3 | 150 | ALN 2.5 mg | Placebo | |
| C1 | 150 | ALN 5 mg | ALN 5 mg | ALN 5 mg |
| C2 | 150 | ALN 5 mg | ALN 5 mg | Placebo |
| C3 | 150 | ALN 5 mg | Placebo | |
| D | 150 | E/P**** | E/P | |

*ALN = alendronate
**OD = Optimal Dose (either 2.5 or 5 mg).
***R = Subsequent randomization for placebo group Years 5 and 6 extension
****E/P = estrogen/pregestin The study is double blind (for women receiving either alendronate or placebo) for the first two years, at the end of which a first analysis is performed. The study remains double blind until each subject reaches the end of the fourth year of study, when the blind is broken for each subject individually. Subjects are informed only whether or not they received active treatment with alendronate, and, if so, whether they were treated for two or four years. Subjects will not be informed of the dose of the study drug. Those subjects who remain in the blinded study for years 5 and 6, and the investigators remain blinded to their treatment allocation during the extension period.

Subjects in Group "A" (See TABLE 2) continue to take blinded placebo for four years. At the end of four years these women will be informed that they had received placebo during Years 1 to 4. They are then given the option to be further randomized (1:1) between blinded placebo and alendronate at the "optimal" dose or to exit the study.

Groups B1 and C1 receive the 2.5 or 5 mg of alendronate, respectively for six years. Groups B2 and C2 will remain on the 2.5 and 5 mg of alendronate, respectively for four years before switching to placebo for the final two years of the study. Those subjects who remain in the study for Years 5 and 6 will be blinded (double blind) regarding their allocation to active drug or placebo for Years 5 and 6. Groups B3 and C3 remain on the 2.5 and 5 mg alendronate, respectively for only two years before switching to placebo for the third and fourth years of the study. They will discontinue study drug after the fourth year.

Subjects in Group D continue the open label estrogen/progestin treatment for four years, after which they will discontinue the study drug after the fourth year.

At the first visit, a member of the study staff performs an oral examination which includes a tooth count in each patient. A similar examination is conducted after 24 months, and every two years thereafter for the remainder of the study.

Fewer patients receiving alendronate (either high dose or low dose) experience tooth loss as compared to controls receiving placebo. Additionally, for those patients who do experience tooth loss, fewer teeth are lost by those receiving alendronate than those receiving placebo. These differences are statistically significant.

EXAMPLE 2

Tooth Loss in Osteoporotic Population

This trial is conducted similarly to that described in Example 1, except that the approximately 2,400 women who are participants are osteoporotic, i.e. have a bone mineral density less than 2.0 standard deviations below peak mean bone mass. Approximately 33% of the patients have a prevalent vertebral fracture at baseline. Randomization is split between placebo and alendronate. The dose of alendronate is 5 mg per day for the first two years, and 10 mg per day for the third year. All subjects who have a calcium intake less than 1,000 mg per day are offered free calcium supplements which provide 500 mg elemental calcium and 250 units of vitamin D.

After three years, fewer patients receiving alendronate experience tooth loss than those receiving placebo. Additionally, for those patients who do loose teeth, fewer teeth are lost by those receiving alendronate than those receiving placebo.

What is claimed is:

1. A method of preventing tooth loss not necessarily associated with periodontal disease comprising administering to a patient an effective amount of alendronate, or a pharmaceutically acceptable salt thereof for a substantial period of time.

2. A method according to claim 1 wherein the alendronate is in the form of monosodium alendronate trihydrate.

3. A method according to claim 1 wherein the alendronate or its pharmaceutically acceptable salt is administered orally.

4. A method according to claim 3 wherein the dosage is 2.5 mg/day to 40 mg/day.

5. A method according to claim 4 wherein the dosage is 2.5, 5, or 10 mg/day.

6. A method according to claim 5 wherein the alendronate is administered substantially daily for at least about 3 years.

* * * * *